United States Patent [19]
Holt et al.

[11] Patent Number: 6,111,973
[45] Date of Patent: Aug. 29, 2000

[54] METHOD FOR PRODUCING COLOR-COMPARABLE PHOTOGRAPHS WITH FLESHTONE COLOR SELECTIONS FOR PROSTHETIC FABRICATION

[76] Inventors: Kenneth Dale Holt; David Michael Holt, both of 6260 W. Highland, Midlothian, Tex. 76065

[21] Appl. No.: 08/864,748

[22] Filed: May 29, 1997

[51] Int. Cl.[7] ........................................... G06K 9/00
[52] U.S. Cl. .................. 382/100; 382/115; 382/165; 356/402
[58] Field of Search .................... 382/112, 165, 382/115, 111, 100; 356/402

[56] References Cited

U.S. PATENT DOCUMENTS

| | | | |
|---|---|---|---|
| 4,249,827 | 2/1981 | DiMatteo | 356/402 |
| 5,144,566 | 9/1992 | Anderson et al. | 382/112 |
| 5,177,694 | 1/1993 | Graham et al. | 382/165 |

Primary Examiner—Matthew C. Bella

[57] ABSTRACT

Disclosed is a method of producing color-comparable photographs with which a prosthetic fabrication artist can determine whether photographs taken of an amputee's extremity are color-true and whether recorded color selections, matching pre-designated areas of the extremity, were accurately chosen. A prosthetic technician, or another skilled in the art, takes color photographs of an amputee's extremity on a duplicate copy of a colored background which has a neutral colored central area and a perimeter band of various human fleshtone or skin colors. The technician matches certain colors in the perimeter color-band to pre-designated areas of the extremity and records them on a color selection diagram. The photographs and color selection diagram are forwarded to the fabricating artist who uses them to determine the proper coloration of a prosthetic restoration by comparing the colored background shown in the photograph with a second duplicate copy of the colored background in the possession of the fabricating artist.

7 Claims, 3 Drawing Sheets

A METHOD FOR PRODUCING COLOR-COMPARABLE PHOTOGRAPHS WITH FLESHTONE COLOR SELECTIONS FOR PROSTHETIC FABRICATION

仕111,973

METHOD FOR PRODUCING COLOR-COMPARABLE PHOTOGRAPHS WITH FLESHTONE COLOR SELECTIONS FOR PROSTHETIC FABRICATION

TECHNICAL FIELD OF THE INVENTION

This invention relates in general to prosthetics, and in particular to a method of producing color comparable photographs which include fleshtone color selections for the cooperative fabrication of anatomically correct prosthetic devices when the amputee is not present for the coloration procedure.

BACKGROUND OF THE INVENTION

One of the most important concerns of an amputee seeking to have an anatomically correct prosthetic restoration fabricated is the final coloration of the prosthesis so that it will adequately match the corresponding uninjured extremity and, therefor, be unnoticed by the general public. However, it a major expense and inconvenience for the amputee if he/she is required to travel long distances to the facility which fabricates the prosthesis. In order to avoid these problems, the amputee must use the services of a local prosthetist who must take photographs of the amputee's corresponding uninjured extremity and choose color samples which match certain areas of the amputee's extremity. These photographs and color sample information are then forwarded to a fabricating facility which specializes in anatomically correct prosthetic restoration. The fabricating artist must use this information to match the color of the prosthesis to the amputee's true extremity color.

If the photographs and color selections are of poor quality due to inadequate film, insufficient lighting, etc., the fabricating artist cannot properly match the prosthesis coloration to the amputee's actual color. The industry, therefore, has a need for an improved method which conveniently and accurately reveals the true color of the extremity on an amputee who is not present during the final coloration process Heretofore, in the cooperative fabrication of anatomically correct prosthetic extremity restorations, it has been the common practice to produce photographs of the amputee's extremeties on a color-key background which includes only the primary or basic colors. Photographs produced from the use of these color-key backgrounds have a number of undesirable aspects. These photographs can only be used to determine whether the color-key background in the photograph is of the same color or shade as the original background, therefore limiting the comparison to the basic colors shown on the background. Also, human skin reflects light at a much different ratio than a flat surface which, in common practice, has a glossy finish. Furthermore, the current methods for selecting color samples requires that the prosthetist selects individual pieces of unmarked material for certain areas of the amputee's skin, mark or tag those pieces, and forward them to the fabricating facility. These pieces of prosthetic material can easily be lost of misnumbered. Another current method involves a collection of numbered prosthetic material swatches requiring that the prosthetist and the fabricator both have duplicate collections of the same prosthetic material swatches. These swatches, usually on a chain, can be cumbersome to use and generally have too few colors from which to make selections. Although these swatches can be discolored by light or chemicals and easily soiled, they are somewhat difficult to replace with exact duplicates since they are generally made in batches. Also, since the fabricating artist usually does not see the amputee, he must depend solely on the prosthetists ability to select colors accurately.

In addition to the aforementioned drawbacks, a photographic film is not available, for practical applications, which will perfectly reproduce the true colors in the actual extremity or colored background. As a result, the photographs received by the fabricating artist are usually too red, too green, etc. Therefore, they are never exactly the color of the amputee's extremity. This makes it necessary for the fabricating artist to estimate how much color adjustment to make based solely on the lack or abundance of the primary or basic colors on the color-key background as shown in the photographs.

SUMMARY OF THE INVENTION

The present invention thus aims at eliminating or reducing these and other drawbacks of known methods of producing color-comparable photographs and making color selections to match pre-designated areas of the human anatomy. For this purpose, there is, according to the invention proposed, a new method of producing said photographs and selections, the characteristic features of which are indicated in the subsequent claims and explained further below.

According to one aspect of the invention, the method of producing color-comparable photographs which include pre-selected color swatches is characterized by the design and production of a colored photography background on paper or any other flat surface suitable for said purpose. In it's preferred design, this colored background will contain, within it's borders, a central area of a neutral color (e.g. gray) whereupon the amputee's uninjured extremity is placed for the color-comparable photographs. This neutral colored central area prevents the undesirable effect of unwanted color reflection of light from the background to the extremity, which can alter the skin color. Surrounding the neutral colored central area, and along the edges of the colored background surface, are numbered fleshtone colored areas (referred to as swatches herein) which are tinted from very light fleshtone colors to very dark. Keeping these swatches to a minimum desirable width, a vast array of fleshtone colors can be incorporated around all four edges of the background surface providing a wide variety of color choices for matching pre-designated areas of the amputee's extremity. Since the fleshtone colors are included within the photographs taken of the amputee's extremity, the fabricating artist can compare the pre-selected and recorded fleshtone colors to pre-designated corresponding areas of the extremity and, thereby, adjust the painting of the prosthetic restoration to compensate for the differences in the color, tint, or shade of the background shown in the photograph by it's comparison to a duplicate copy of the colored background which is in the possession of the fabricating artist.

According to another aspect of the invention, a method of recording individual color swatch numbers corresponding to pre-designated areas of the amputee's extremity is provided as an integral part of the color-comparable photograph and color selection system. With this system, the technician skilled in the art, working with the amputee, selects individual color swatch numbers which correspond to certain pre-designated areas on the amputee's extremity. These color swatch numbers are recorded on a color selection diagram specifically designed to indicate certain areas of the extremity which reveal a variety of colors in the extremity. When the fabricating artist receives this information recorded on the color selection diagram along with the color-comparable photographs of the amputee's extremity adjacent to the recorded color swatches, the artist can use this information to immediately determine whether the photograph is color-true and was properly exposed. Also, since the pre-selected color swatches are automatically included in the photographs adjacent to the amputees extremity, a person skilled in the art can easily determine whether the selections are accurate.

According to another aspect of the invention, the tint of the color-comparable photographs can be altered by adding colored light from the flash or surrounding light sources, during the photography process, in order to compensate for a type of film which may cause the photographs to have too much of a certain color such as red, blue, yellow, etc. In practical application, this can easily be achieved by reflecting the light of the camera flash off a surface which is colored to reflect the desired light color addition to the photograph. As an example, if the photographer is using a film which is known to develop into a photograph which has too much green tint (a common effect), a lavender colored surface can be used to reflect light which will help cancel the green effect, thereby, adjusting the photographs back to a more true color. Another method for adding colored light is to place a transparent colored plastic film over the camera flash when the taking the photograph.

In summary, it is the primary objective of this invention to provide a more accurate and convenient method of producing color-comparable photographs and making color selections for the purpose of cooperative prosthetic fabrication between two separate facilities when the amputee is not present for the coloration procedure.

These, together with other objects and advantages, will become apparent to those skilled in the art upon reading the details of the method which are more fully set forth below.

DETAILED DESCRIPTION OF THE INVENTION

Figure 1:
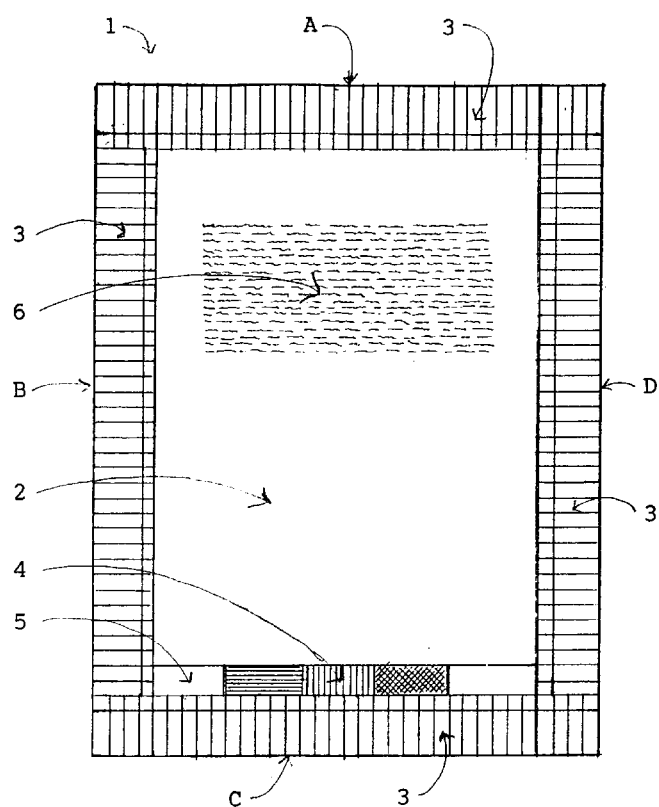
FIG. 1 illustrates one of many possible configurations of the colored background used to produce color-comparable photographs and to make a variety of color selections.

Referring to the drawings, there are shown the steps in preparing color-comparable photographs and making color swatch selections according to the invention For purposes of example only, the method will be described in connection with the fabrication of a prosthetic hand by the illustration of the production of said photographs and color selections of an uninjured hand.

As shown in FIG.1, a colored background (1) is made on a flat surface (preferably non-glossy) of any material which can receive and maintain the colors which are printed on said surface. This surface (1) will contain, on a central area (2), a neutral color (e.g. gray) whereupon the amputee's uninjured extremity (20) is placed for a series of photographs, some positions of which are shown in FIGS. 3(a)–3(d). The colored background (1) is colored, around the perimeter between the neutral colored central area (2) and the outer edges of the colored background (1), with a variety of human fleshtone colors (3) ranging from light colors (e.g. Caucasian) to dark colors (eg. African-American). This variety of human fleshtone colors (3) hereafter referred to as color-band (3)) contains individual color areas of sufficient size so as not to cause confusion of the colors when viewed at a normal working distance (as indicated in FIG. 4), yet of a small enough size to allow space for a large variety of colors. It is important to have as many color swatches in the color-band (3) as is practical since the variety of human fleshtone colors is very broad.

FIG. 1 also shows a second color-band (4) between the neutral colored central area (2) and the bottom outer color-band (3). This second color-band (4) includes the three primary colors (red, yellow, and blue) for the purpose of clearly indicating the difference in tint between the colored background (1) shown in the developed photograph and the fabricating artist's duplicate copy of the colored background (1). The second color-band (4) also includes one or more swatches of pure white (5) which are for the purpose of indicating the abundance or lack of light available when the photograph was taken. This information helps the fabricating artist determine how much darker or lighter the finished prosthesis should be in relation to the color-comparable photographs.

For the convenience of the user, the colored background (1) in FIG. 1 includes detailed instructions (6) describing how to take color-comparable photographs in accordance with the invention. The top, left, bottom and right edges of the colored background (1) are marked (A),(B),(C) and (D) respectively for the purpose of orientation in FIGS. 3(a)–3(d).

Figure 2:
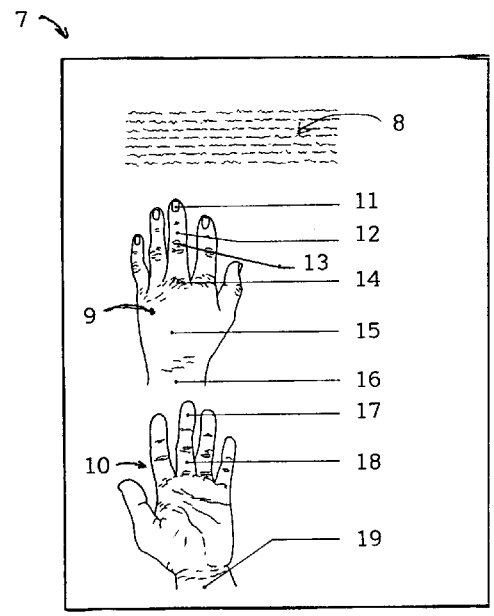
FIG. 2 shows one of many possible configurations of a color selection diagram used in conjunction with the colored background shown in FIG. 1.

As shown in FIG. 2, a color selection diagram (7) is made on which the user records the numbers of the color swatches from the color-band (3) which most closely match the areas (11–19) indicated on the drawings of each side of the hand (20). Detailed instructions (8) are included on the color selection diagram (7) along with drawings of the dorsal view of a hand (9) and the palmar view of a hand (10). The two views of the hand have lines drawn from pre-designated areas (11–19) of each hand view (9–10) to blank lines which are to be filled in with the numbers corresponding with the color swatches in the color-band (3) which most closely match each individual pre-designated area (11–19). The areas of the hand which need to have separate color matches recorded are: the darkest color in the fingernails (11), the lightest color between the PIP and the DIP joints in the fingers (12), the darkest color in the PIP joint of the fingers (13), the darkest color in the MCP joint of the fingers (14), the average color of the central dorsal area (15), the average color of the arm above the wrist on the dorsal side (16), the darkest color of the fingertip pad on the palmar side (17), the darkest color of the palmar side finger between the PIP and the DIP joints (18), and the average color of the arm just above the wrist on the palmar side (19).

Figure 3A:
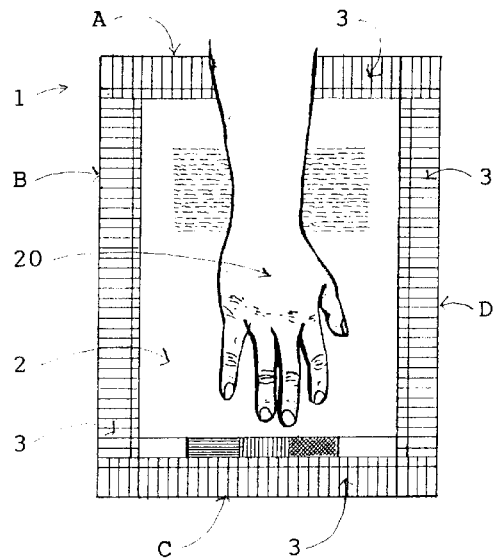
FIGS. 3(a), 3(b), 3(c) and 3(d) are illustrative of the various positions in which the amputee's extremity is placed on the colored background of FIG. 1 for a series of certain photographs of the method.
Figure 3B:
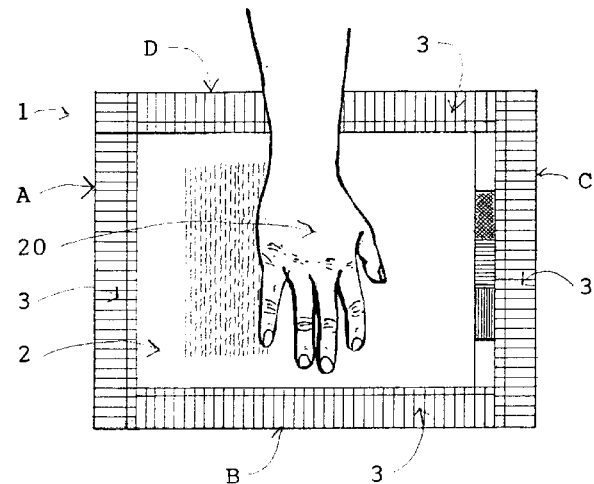
Figure 3C:
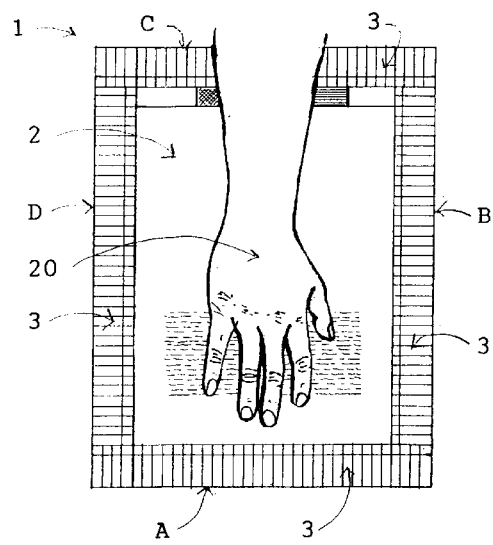
Figure 3D:
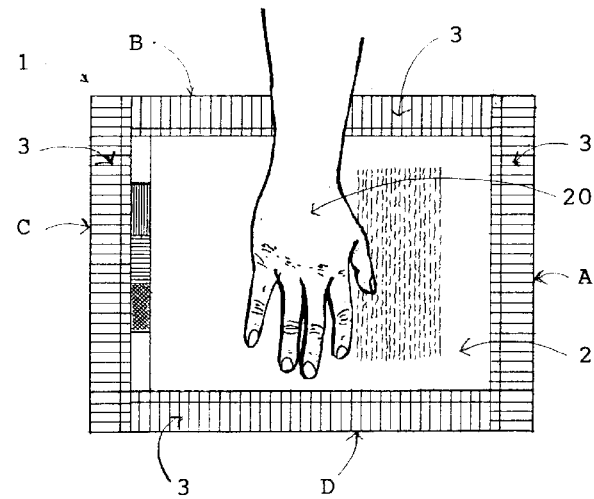
Figure 4:
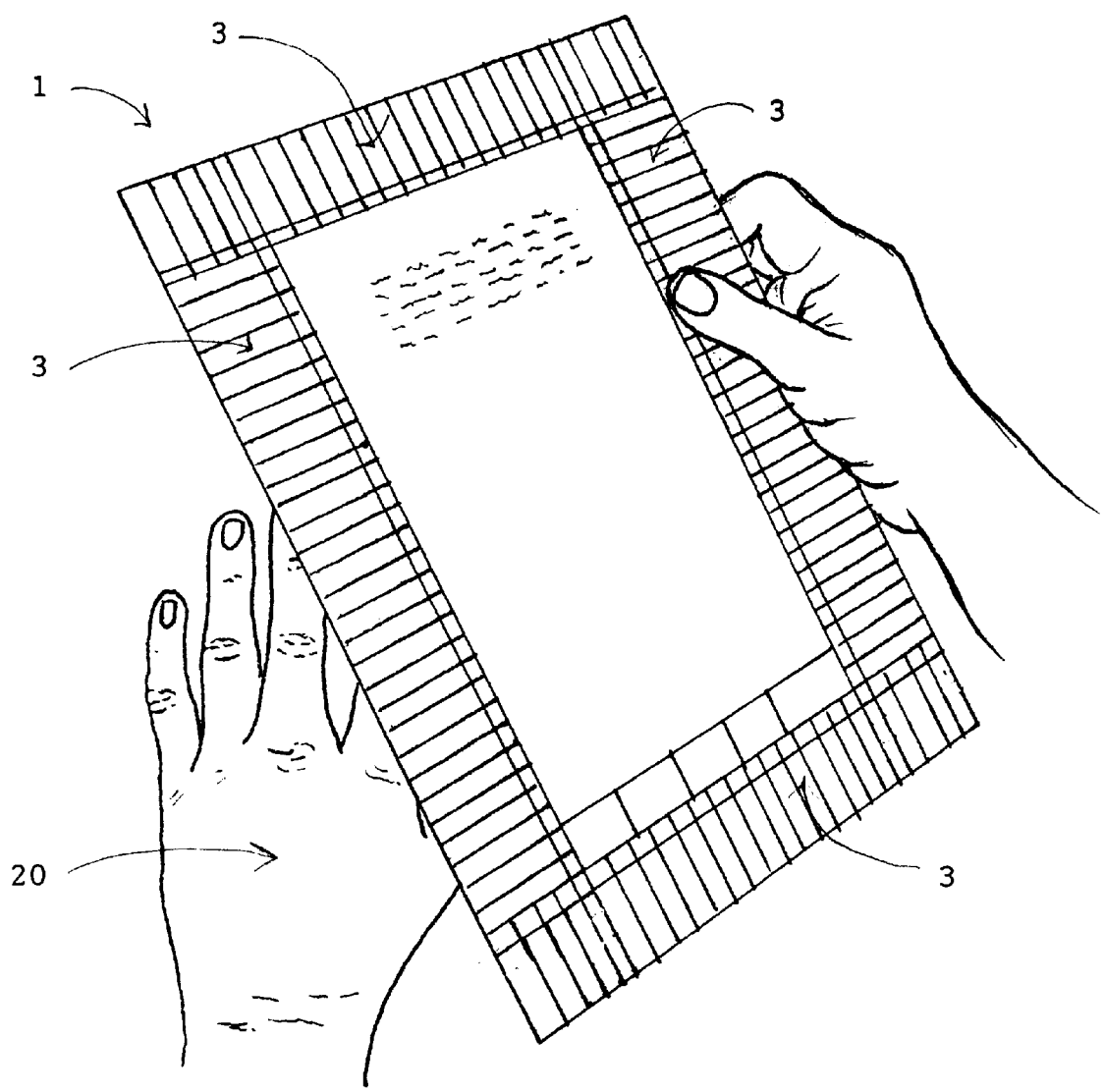
FIG. 4 illustrates the colored background in it's additional use of making color swatch selections from the same colored background on which the photographs are taken.

To begin the steps of the invention involving the amputee, the person skilled in the art instructs the amputee to rest the extremity (20) on the neutral colored central area (2) of the colored background (1) with the fingertips adjacent to the second color-band (4) and the fleshtone color-band (3) along the bottom edge (C) as shown in FIG. 3(a). After the extremity has rested on the colored background (1) for approximately 30 seconds to allow blood circulation to stabilize, the photographer snaps the photograph of the extremity (20) on the colored background (1). After rotating the colored background (1) 90 degrees, as is shown in FIG. 3(b), a second photograph is taken of the extremity (20) with the fingertips now adjacent to the fleshtone color-band (3) along the edge (B). After rotating the colored background (1) again as shown in FIG. 3(c), a third photograph is taken of the extremity (20) with the fingertips now adjacent to the fleshtone color-band (3) along the edge (A). Again, after rotating the colored background (1) 90 degrees as shown in FIG. 3(d), a fourth photograph is taken of the extremity (20) with the fingertips now adjacent to the fleshtone color-band (3) along the edge (D).

The steps of the invention involving the photography of the extremity (20) to produce a series of color-comparable photographs as described above and shown in FIGS. 3(a)–3(d) are repeated with any other desired position or angle of the extremity (20).

All color-comparable photographs are taken as close-up as possible making sure that the entire color-band (3) along the edge adjacent to the fingertips of the extremity (20) is visible in the frame of the developed photograph.

If the available 1light from outdoors or indoors is insufficient for proper film exposure, a flash is used to provide additional light However, it is important to diffuse the light so that it is evenly spread over the entire colored background (1). The light of the flash can be diffused by bouncing it off a large white flat surface (e.g. poster board) held two to three feet above the colored background (1) and angled so that the light from the flash is reflected to spread vertically and evenly over the photographed area. Using this same procedure, one skilled in the art can adjust the tint of the developed photograph by substituting a colored flat surface instead of white, thus providing a means of compensating for a type of camera film that does not develop into a color-true photograph (a common problem).

In accordance with the invention, the colored background (1) is also used to select numbered color swatches from the color-band (3) which match pre-designated areas (11–19) of the amputee's extremity (20). As is shown as an example in FIG. 4, selecting the corresponding numbers of the color swatches is accomplished by holding the colored background (1) so that the color-band (3) with the fleshtone colors is adjacent to one of the pre-designated areas (11–19) on the amputee's extremity. The technician (of FIG. 4) is seeking to find and record the number of the closest matching color swatch for the area between the PIP and the DIP joint (12) on the dorsal side of the hand (9). The technician, or other person skilled in the art, places the colored background (1) on the designated area (12) so that the fleshtone color-band (3) is adjacent to the area (12) to be matched. He then moves the color-band (3) along the area (12) (rotating to all four sides if required) until the color swatch is located which most closely matches the designated area (12). When the closest match is found, the number assigned to the matching color swatch is recorded on the blank assigned for that particular area (12). The same procedure is used to record the color swatch numbers for all other designated areas (11–19). With this color swatch matching and recording system, the fabricating artist does not have to rely solely on the color-comparable photographs. The numbers of the color swatches, therefore become an additional cross-reference used to determine the proper color for the painted prosthesis.

After the fabricating artist receives the color-comparable photographs and color matching information from the cooperating technician, the photographs are carefully compared to an exact duplicate copy of the colored background (1) in the possession of the fabricating artist If the photographs are found to be lacking a certain color, the fabricating artist who is skilled in the art can estimate how much of the lacking color to add to the painted prosthesis to assure a close color match with the amputee's uninjured extremity. The fabricating artist also has the option of adding additional colored light to the viewing area to adjust the appearance of the colored background (1) in the photograph until it closely matches the fabricating artist's duplicate copy of the colored background (1). The colored light addition can easily be accomplished by placing a transparent colored plastic film over a light fixture which is directed at the color-comparable photograph.

It can be seen from the foregoing that an improved technique has been provided for producing color-comparable photographs combined with making color match selections in the field of prosthetics. Now, an amputee who is unable to travel to the facility of an anatomically correct prosthetic restoration fabricator can be provided with a prosthetic restoration with a very close color match, even though the amputee is not present during the final painting process. It should be understood, however, that the foregoing is only exemplary of certain techniques utilized in the remote cooperative fabrication of anatomically correct prosthetic restorations. These techniques may be employed to provide means for remote fabrication of any external member of the human anatomy susceptible to artificial fabrication (e.g. hands, fingers, feet, toes, ears, noses, etc.).

The specific techniques and embodiment disclosed herein are intended to be merely exemplary of the invention and not restrictive thereof since various modifications readily apparent to those skilled in the art can obviously be made without departing from the spirit and scope of the invention as claimed herein below.

What is claimed is:

1. A method for producing color-comparable photographs which include the view of recorded, visually selected skin color matches of an amputee's uninjured limb extremity for the substantial identical coloration of an anatomically correct prosthetic restoration for the amputee's injured limb extremity in the absence of the amputee, comprising the steps of:

producing a colored photography background on a flat surface including a neutral colored central area such as gray, and a multi-colored outer band around the perimeter of the flat surface containing a variety of individually numbered human skin fleshtone colors ranging from light skin colors to dark skin colors;

producing duplicate copies of the colored photography background;

delivering a first duplicate copy of the colored photography background to at least one cooperating technician responsible for photographing the amputee's limb extremity in a first location;

visually selecting individually numbered skin colors from the perimeter multi-colored band which closely match pre-designated areas on the amputee's uninjured limb extremity;

recording the color selections so that each color number corresponds to the pre-designated areas on the amputee's uninjured limb extremity;

placing the amputee's uninjured limb extremity atop the surface of the first duplicate copy of the colored background adjacent to the perimeter band of skin colors;

photographing the uninjured limb extremity while it rests on the surface of the first duplicate copy of the colored background;

delivering the developed photographs of the limb extremity shown atop the first duplicate copy of the colored background along with the recorded color selection numbers to a fabricating artist in a second location;

comparing the photographs of the uninjured limb extremity as shown atop the first duplicate copy of the colored background to a second duplicate copy of the colored background;

comparing the recorded color selections as they appear on the second duplicate copy of the colored background to the corresponding pre-designated areas on the uninjured limb extremity shown in the photograph;

utilizing the comparison of the first duplicate copy of the colored background shown in the photograph with the second duplicate copy of the colored background as a means to determine the color and/or shade accuracy of the photographs; and utilizing the comparison of the recorded color selections as they appear on the second duplicate copy of the colored background to the corresponding pre-designated areas on the uninjured limb extremity shown in the photographs as a means to determine the correct coloration of an anatomically correct prosthetic limb restoration device for attachment to an amputee's injured limb extremity.

2. The method of claim 1 wherein the colored background includes a color-band with medium shades of the three basic primary colors; red, blue and yellow.

3. The method of claim 1 wherein the colored background is printed on a surface with a matte finish.

4. The method of claim 1 further including rotating the colored background for a series of photographs with the limb extremity at rest on the neutral colored central area adjacent to different multi-colored perimeter bands of the colored background in each photograph.

5. The method of claim 1 further including the addition of colored light while taking the photograph for the purpose of altering the color of the developed photograph.

6. The method of claim 1 further including the addition of colored light while viewing the developed photograph for the purpose of adjusting the perceived color of the first duplicate copy of the colored background shown in the photograph to match the second duplicate copy of the colored background.

7. The colored photography background according to claim 1 for the purpose of producing color-comparable photographs and making a record of visually matched human skin fleshtone colors to be used in prosthetic limb extremity restoration fabrication.

* * * * *